United States Patent [19]

Conway et al.

[11] Patent Number: 5,320,827
[45] Date of Patent: Jun. 14, 1994

[54] ENCAPSULATED ALUMINUM-ZIRCONIUM COMPOSITIONS

[75] Inventors: Lori J. Conway, Hope; Dimitris E. Katsoulis; William J. Schulz, Jr., both of Midland, all of Mich.

[73] Assignee: Dow Corning Corporation, Midland, Mich.

[21] Appl. No.: 73,194

[22] Filed: Jun. 8, 1993

Related U.S. Application Data

[60] Division of Ser. No. 742,671, Aug. 7, 1991, abandoned, which is a continuation-in-part of Ser. No. 631,308, Dec. 21, 1990, abandoned.

[51] Int. Cl.$^5$ .................. A61K 7/34; A61K 9/12
[52] U.S. Cl. .................. 424/47; 424/DIG. 5; 424/66; 424/401
[58] Field of Search .................. 424/47, DIG. 5, 68

[56] References Cited

U.S. PATENT DOCUMENTS

| | | | |
|---|---|---|---|
| 4,524,062 | 6/1985 | Laba et al. | 424/65 |
| 4,803,195 | 2/1989 | Holzner | 512/4 |
| 4,818,522 | 4/1989 | Ferentchak | 424/66 |

FOREIGN PATENT DOCUMENTS

| | | | |
|---|---|---|---|
| 0303461 | 10/1988 | European Pat. Off. | A61K 7/32 |
| 6049285 | 10/1986 | Japan | A61K 7/32 |

OTHER PUBLICATIONS

S. Cohen, et al.; J. Am. Chem. Soc. 1990; "Ionically Cross-Linkable Polyphosphazene: A Novel Polymer for Microencapsulation"; 112, pp. 7832-7833.

R. Dagani; C&EN; "Polyphosphazene Encapsulates Living Cells"; Oct. 22, 1990, p. 28.

*Primary Examiner*—Dale R. Ore
*Attorney, Agent, or Firm*—Sharon K. Severance

[57] ABSTRACT

Encapsulated aluminum-zirconium salt compositions are produced by combining and heating an aqueous aluminum-zirconium salt selected from aluminum-zirconium halohydrates and mixtures thereof; a hydrophobic liquid; and a carboxylate. The mixture is heated until substantially all of the free water has been removed. The encapsulated aluminum-zirconium salts precipitate out after the removal of the water. The encapsulated aluminum-zirconium salts are useful in deodorant and antiperspirant compositions.

4 Claims, No Drawings

ENCAPSULATED ALUMINUM-ZIRCONIUM COMPOSITIONS

This is a divisional of copending application(s) Ser. No. 07/742,671 filed on Aug. 7, 1991 which is a continuation-in-part of Ser. No. 07/631,308 both now abandoned.

This invention pertains to encapsulated aluminum-zirconium halohydrate compounds. An aluminum-zirconium halohydrate salt is encapsulated in a shell comprising a carboxylate, such as stearic acid. The aluminum-zirconium salts are released from the encapsulant in the presence of moisture and are useful in antiperspirant and deodorant compositions.

BACKGROUND OF THE INVENTION

It is known in the art to coat or encapsulate certain materials to provide a protective barrier to the material and/or to control the release characteristic of the material. A coated material is typically surrounded by a film wherein the film is "adhered" to the composition. An encapsulated material is typically surrounded by a film in the form of a shell or capsule wherein the shell or capsule is not necessarily adhered to the composition.

Topically applied materials such as cosmetics, lotions, fragrances, antiperspirants and deodorants, which contain ingredients that are encapsulated or coated, are known in the art. For example, Japanese Patent No. 86049285 teaches a transparent cosmetic composition comprising a fine powdered mica which is coated with a mixture of a hydrocarbon, a fatty acid, and a silicone oil and then baked at 100° C. to 150° C. for 1 to 5 hours. The coated mica gives a transparent appearance and soft brilliance to skin.

In antiperspirant or deodorant compositions, it is known to encapsulate or coat a deodorant active or a fragrance added to the deodorant or antiperspirant composition however, it is virtually unknown to encapsulate antiperspirant actives.

U.S. Pat. No. 4,803,195 to Holzner teaches a personal care composition having deodorant or antiperspirant activity comprising the deodorant or antiperspirant active and a perfume base wherein the perfume base is either in the form of an aqueous emulsion or in microencapsulated form. The perfume is released upon contact with moisture and can be re- encapsulated in situ.

U.S. Pat. No. 4,818,522 to Ferentchak et al. teaches antiperspirant compositions comprising water-immiscible adjuvants which are encapsulated in thick-walled, hallow, substantially spherical particles of an antiperspirant active. The water immiscible adjuvants include fragrances, antibacterials, antimicrobial or antifungal agents, deodorants or other dermatological preparations. The antiperspirant actives are the encapsulant material therefore Ferentchak et al. does not teach a method for encapsulating antiperspirant actives. The encapsulated water-immiscible adjuvants are prepared by emulsifying the adjuvant in an aqueous solution of the antiperspirant active and spray drying the resulting material.

EP Patent No. 0303461 to Wright teaches antiperspirant and deodorant compositions containing moisture sensitive capsules which in the presence of moisture release sensory agents such as perfumes, skin coolants, emollients or other benefit agents such as deodorant actives, antiperspirant actives, and anticholinergic actives. The special polymer from which the capsules are formed is preferably a polysaccharide. The method for preparing the capsules comprises preparing an emulsion of water, the special polymer and the sensory or benefit agent and spray drying the emulsion. The only benefit obtained through the encapsulation of the antiperspirant active is believed to be the ability to produce stable alcoholic compositions and release of the agent in the presence of moisture.

U.S. Pat. No. 4,524,062 to Laba et al. teaches an antiperspirant/deodorant stick composition which comprises a powdered antiperspirant active, a coating material for the antiperspirant active, a deodorant and a cologne stick base. The coating material is typically a glycol stearate and the coated antiperspirant active is achieved by blending the antiperspirant active and the glycol stearate at a temperature at which the glycol stearate is a liquid. U.S. Pat. No. 4,524,062 does not teach a process for obtaining the antiperspirant active in an encapsulated form and there is no evidence to show that the antiperspirant active is even coated and not merely suspended in the glycol stearate.

It is an object of this invention to show encapsulated aluminum-zirconium halohydrate compositions.

It is further an object of this invention to show a method for producing the encapsulated aluminum-zirconium halohydrate compositions.

It is further an object of this invention to show a method for producing encapsulated aluminum-zirconium halohydrate compositions of a controlled particle size and shape.

It is further an object of this invention to show deodorant and antiperspirant compositions comprising the encapsulated aluminum-zirconium salt.

THE INVENTION

The encapsulated aluminum-zirconium salts of this invention are comprised of aluminum-zirconium halohydrate contained in a shell comprised of a carboxylic acid or carboxylic acid derivative (herein referred to as carboxylate). Upon contact with moisture, the shell opens up and releases the aluminum-zirconium halohydrate. Some or all of the aluminum-zirconium halohydrate may be dissolved in the moisture, depending on the concentration of the salt and the amount of moisture.

The encapsulated aluminum zirconium salts of this invention are produced by combining together, with agitation, an aqueous aluminum-zirconium halohydrate salt, a non-water miscible hydrophobic liquid (herein referred to as hydrophobic liquid), and a carboxylate and heating the mixture to a temperature sufficient to remove substantially all free water. Some of the hydrophobic liquid may be removed during the heating because of an azeotrope that may form between the hydrophobic liquid and the water. It is important that the rate of water distillation be faster than the rate of hydrophobic liquid distillation. It is preferred that any azeotrope formed contain more than 50% by weight of water. After the removal of the water, the encapsulated aluminum-zirconium salts precipitate out of the reaction medium. Typically, an increase in the temperature will occur when the distillation of the aqueous phase is complete. Upon completion of the distillation there should be enough fluid remaining to keep the encapsulated aluminum-zirconium salts free flowing. The encapsulated aluminum-zirconium salts can then recovered through separation means such as filtration.

The aqueous aluminum-zirconium halohydrates useful in the instant invention are those currently known in the art. The aluminum-zirconium halohydrates may be exemplified by aluminum-zirconium chlorohydrate, aluminum-zirconium bromohydrate, and aluminum-zirconium iodohydrate and mixtures thereof. The aluminum-zirconium halohydrates are typically buffered with an amino acid such as glycine. The aluminum-zirconium halohydrates useful in the instant invention may be further described as a standard (non-activated) or an activated salt. An activated salt, through compositional differences, is more efficacious when used in antiperspirant compositions.

The aluminum-zirconium halohydrates useful in the instant invention may be further described by the formula $$Al_aZr_b(OH)_cX_d$$

where a/b has the value of 0 to 20, b has a value of treater than 0, $3a+4b=c+d$; and X is selected from Cl, Br, I and $NO_3$.

The aluminum-zirconium halohydrate may be supplied as an aqueous solution containing greater than 0% by weight of the aluminum-zirconium halohydrate. The maximum amount of aluminum-zirconium halohydrate in the aqueous solution is dependent upon its solubility in water. Typically the aluminum-zirconium halohydrate is used as an aqueous solution comprising 10% to 40% by weight of the aluminum-zirconium halohydrate. Aqueous solutions containing less than 10% by weight of the aluminum-zirconium halohydrate may be used to produce an encapsulated aluminum-zirconium salt, however, they are not economically advantageous. Aqueous solutions containing greater than 40% by weight of the aluminum- zirconium halohydrate are not well known in the art however, they are useful when obtainable.

Non-water miscible hydrophobic liquids useful in the instant invention may be selected from low viscosity silicone fluids, paraffin oils such as mineral oil, and mixtures thereof. The low viscosity silicones and further, low viscosity cyclic siloxanes are the preferred hydrophobic liquid.

Low viscosity silicones useful in the instant invention are selected from cyclic and linear silicones and mixtures thereof which have a viscosity of less than 1,000 centistokes. The cyclic low viscosity silicones may be exemplified by compounds having the formula

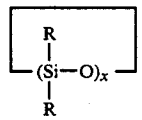

wherein each R is independently selected from an alkyl group containing 1 to 30 carbon atoms and an aryl group containing 6 to 10 carbon atoms and x has the value of 3 to 10. The preferred cyclic low viscosity silicone is when R is predominantly methyl and x is 4 to 5.

The cyclic low viscosity silicones may be further exemplified by, but not limited to hexamethylcyclotrisiloxane, octamethylcyclotetrasiloxane, decamethylcyclo- pentasiloxane, dodecamethylcyclohexasiloxane and mixtures thereof.

The linear low viscosity silicones may be exemplified by compounds having the formula

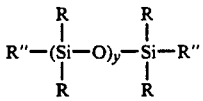

wherein each R is independently selected from an alkyl group containing 1 to 3 carbon atoms and an aryl group containing 6 to 10 carbon atoms: R" is selected from R and a hydroxyl group (—OH); and y has the value such that the viscosity of less than 1,000 centistokes. The preferred linear low viscosity silicone is when R is predominantly methyl.

The linear low viscosity silicones may be further exemplified by, but not limited to, trimethylendblocked dimethylpolysiloxane fluids. 5, 10. 25 and 50 cS dimethylpolysiloxane fluids, octamethyltrisiloxane, decamethyltetrasiloxane, hydroxyl endblocked polydimethylsiloxanes, and mixtures thereof.

The carboxylates useful in the instant invention are selected from the group consisting of carboxylic acids, alkali metal carboxylates, glyceryl carboxylates, carboxylic acid anhydrides, carboxylic acid chlorides and mixtures thereof. The carboxylates useful in the instant invention may be further exemplified by the formulas:

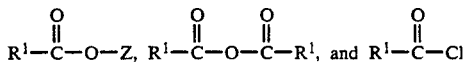

wherein $R^1$ is selected from the group consisting of a saturated or unsaturated, branched or linear alkyl group consisting of at least 2 carbon atoms and a substituted or unsubstituted phenyl group consisting of at least 6 carbon atoms; and Z is selected from the hydrogen atom, alkali metals, and glyceryl. $R^1$ may be further exemplified by, but not limited to, ethyl, propyl, octyl, decyl, undecyl, pentadecyl, hexadecyl, octadecyl, doeicosyl, phenyl, phenyl ethylene, and others. Z may be further exemplified by, but not limited to, the hydrogen atom, sodium, potassium, —$CH_2CH(OH)CH_2OH$, and —$CH(OH)CH_2OH$.

For the carboxylates to be useful in the instant invention it is necessary for the carboxylate to be soluble in the hydrophobic liquid and/or to have a melting point less than the water distillation temperature and further, the carboxylate must not be completely distillable at the water distillation temperature. When using a carboxylate where Z is an alkali metal it may be necessary to add a co-solvent, such as water, to completely dissolve the alkali metal carboxylate.

The carboxylates useful in the instant invention may be further exemplified by, but are not limited to, butyric acid, caprylic acid, lauric acid, palmitic acid, stearic acid, isostearic acid, behenic acid, oleic acid, linoleic acid, linolenic acid, phenylacetic acid, sodium stearate, sodium palmitate, potassium stearate, glyceryl monostearate, stearic anhydride, palmitic anhydride, lauric anhydride, stearoyl chloride, myristyoyl chloride, octanoyl chloride and mixtures thereof. The preferred carboxylate is stearic acid due to it being a cosmetically acceptable ingredient and it has the acceptable properties to make it useful.

The encapsulated aluminum-zirconium salts are formed by combining at least 14 millimoles of carboxylate for every 100 parts of aluminum-zirconium halohydrate solids, and at least 1 part of hydrophobic liquid for every part of water. It is preferred to use between 35 to 200 millimoles of carboxylate per every 100 parts of aluminum-zirconium halohydrate solids and at least 1.25 parts hydrophobic liquid per every part of water. It may be possible to use less than one part of hydrophobic liquid for every part of water if the amount of hydrophobic liquid lost in the distillation azeotrope is replaced during the encapsulation.

The aqueous aluminum-zirconium halohydrate, carboxylate and hydrophobic liquid are combined and heated, with agitation, to a temperature sufficient to remove substantially all of the free water from the solution (water distillation temperature). Typically temperatures greater than 100° C., preferably 100° to 130° C., at atmospheric pressure are useful for removing any water. When the water has been removed the temperature will rise above the water distillation temperature. It is preferred that the temperature does not exceed 150° C. for an extended period of time. Temperatures which exceed 150° C. for an extended period of time may be detrimental to the encapsulant and lead to fragmentation or cracking of the shell and possibly the conversion of the aluminum-zirconium halohydrate into an aluminum-zirconium oxide. Pressures greater or less than atmospheric pressure can be employed in the method of the instant invention thereby allowing the mixture to be heated to higher or lower temperatures for the removal of the water. It is essential that the water be removed during the heating step. Merely heating to temperatures greater than 100° C. while refluxing, or containing the water otherwise, will not result in an encapsulated aluminum-zirconium salt. Typically, the completion of the water removal will be indicated by an increase in the temperature above the water distillation temperature.

After the removal of the water from the mixture, the encapsulated aluminum-zirconium salts precipitate out of the reaction medium. The encapsulated aluminum zirconium salts are typically recovered from the reaction medium by filtration means such as gravimetric, pressure or vacuum filters or by other separation means such as decanting or centrifuging. Filtration means will vary depending on the batch size. It is preferred to recover the encapsulated aluminum-zirconium salts from the reaction medium at a temperature at or above the temperature at which the carboxylate is a liquid. It is further preferred to recover the encapsulated aluminum-zirconium salts from the reaction medium using filtration means.

After the encapsulated aluminum-zirconium salts have been recovered by filtration means from the reaction medium, they may be optionally washed using a hydrophobic solvent to remove any excess carboxylate that might be adhered to the shells. If the carboxylate is not a liquid at room temperature it may be necessary to heat the hydrophobic liquid to a temperature at which the carboxylate is a liquid during the wash.

It is theorized that the shell material of the encapsulated aluminum-zirconium salt is comprised of mostly carboxylate, however, it may contain some hydrophobic liquid which may have been entrapped within the coating. Further, it is theorized that the shell comprises less than 5% and more likely less than 1% of the total encapsulated aluminum- zirconium salt mass. It is further theorized that the coating thickness is dependent upon the concentration of the carboxylate used. Typically the shells are spherical in nature however, they may also be elliptical, elongated or shaped otherwise. The standard aluminum-zirconium halohydrate salts do not appear to undergo a compositional change during the encapsulation process based on High Performance Liquid Chromatography (HPLC).

The aluminum-zirconium halohydrates do not appear to be released from within the shell in any solvent or liquid except water or solvents containing water. In the presence of water the shells open up releasing the aluminum-zirconium salt and some or all of the aluminum-zirconium salt may be dissolved in the water depending on the amount of water present. Certain solvents such as paraffin oil, toluene, ethanol, hexanes, propylene glycol, isopropyl myristate, and silicone glycol copolymers, did not appear to affect the shell or release the salt.

Another aspect of this invention is the ability to produce encapsulated aluminum-zirconium salts having a controlled particle size and shape. This aspect is accomplished by control of the concentration of the carboxylate and control of the agitation rate. The encapsulated aluminum-zirconium salts of this invention are produced using 15 or more millimoles of carboxylate per every 100 parts aluminum-zirconium halohydrate solids. As the amount of carboxylate used increases, the beads formed become more spherical in shape and uniform in size. Thus, the use of higher amounts of carboxylate may result in uniform, spherical beads.

Particle size distribution is controlled by the agitation rate (the rate of agitation during the water distillation). Encapsulated aluminum-zirconium salts which resemble impalpable powder (5 to 75 microns) can be produced at higher agitation rates. Because of equipment differences, mixing characteristics and other factors, it is not possible to specify an exact agitation rate that will produce an exact particle size however, one skilled in the art would be able to determine this for a specific apparatus.

The encapsulated aluminum-zirconium salts of the instant invention are useful in deodorant and antiperspirant compositions such as aerosols, roll-ons, and sticks. It is preferable for the deodorant and antiperspirant compositions to be anhydrous, however, it is not necessary.

The aerosol compositions are typically comprised of 1 to 20% by weight, preferably 8 to 12 wt. %, of an encapsulated aluminum-zirconium salt; 50 to 90% by weight of a propellant, such as butane, isobutane, propane, nitrogen, carbon dioxide; and 5 to 15% by weight of an anhydrous carrier such as cyclomethicone and ethanol. Optional ingredients, such as cyclomethicone, dimethicone, isopropyl myristate, isopropyl palmitate, fragrance, valve lubricants, talc, silica, suspending aids, polar activators, deodorants and others may be added into the aerosol compositions to improve the aesthetics or to change the characteristics of the propulsion. The aerosol compositions are produced using methods known in the art.

The roll-on compositions are typically comprised of 1 to 20% by weight, preferably 10 to 25 wt. % of an encapsulated aluminum-zirconium salt; 60 to 95% by weight of a carrier liquid, such as water, cyclomethicone, organic esters and derivatives of organic esters, dioctyl adipate and others; and optionally 0.1 to 5% by weight of a suspending aid or 0.1 to 10% by weight of an emulsifier, such as glycerol monostearate, steareth-2, alkoxylates and others. If a suspending aid is used 0.1 to 2% of a polar activator must also be added. Other optional ingredients, such as fragrance, deodorants, talc, silica, polyethylene, silica, dimethicone, aluminum sulfate, starch, octenyl succinate and others, may be added into the roll-on compositions to improve the aesthetics or increase the viscosity of the composition. The roll-on compositions are produced using methods known in the art.

The stick compositions are typically comprised of 1 to 20% by weight, preferably 15 to 25 wt. % of an encapsulated aluminum-zirconium salt; 20 to 65% by weight of a carrier fluid such as cyclomethicone, ethanol or propylene glycol; and 5 to 30% by weight of a gellant such as cetyl alcohol, stearyl alcohol, or hydrogenated caster oil. Optional ingredients, such as organic esters, organic ethers, dimethicone, emulsifiers, talc, silica, fragrance, deodorant, polyethylene and others, may be added to the stick compositions to improve the aesthetics or application of the encapsulated aluminum zirconium salt. The stick compositions are produced using methods known in the art.

Deodorant and antiperspirant compositions such as pump sprays, creams, lotions and others may also formulated with the encapsulated aluminum-zirconium salts.

So that those skilled in the art can understand and appreciate the invention taught herein, the following examples are presented, it being understood that these examples should not be used to limit the scope of this invention over the limitation found in the claims attached hereto.

The term "parts" employed herein refers to parts by weight.

Particle Size Analysis: The particle size of the encapsulated aluminum-zirconium salts was determined by using a Malvern 3600 EZ particle sizer. For analysis, the encapsulated salts were suspended in a solvent selected from cyclomethicone or toluene and the stir speed was set at 4.

Physical Characteristics: The physical characteristics of the encapsulated aluminum-zirconium salts (shape, cracks, jagged edges, etc.) was determined by observing the encapsulated aluminum-zirconium salts under a 40× microscope.

Some of the encapsulated and unencapsulated aluminum-zirconium salts were analyzed by HPLC according to the method taught in European Patent Application 0 256 831, herein incorporated by reference. Sample preparation for the encapsulated aluminum-zirconium salts comprises weighing 1.0 gram of the encapsulated aluminum-zirconium salt into a vial and adding 0.01N HCl to the vial until the total sample weight is 10 grams. The sample is shaken. 2 to 3 ml of the liquid are drawn off and filtered through a 0.45 micron syringe filter. The injected sample size is 2.0 microliters. In the instant application, Peak 4 corresponds with Band III, Peak 3 corresponds with Band 11 and Peak 2 corresponds with Band I as defined in European Patent Application 0 256 831.

EXAMPLE 1

300 grams of a mixture comprised of octamethylcyclotetrasiloxane and decamethylcyclopentasiloxane and 9.9 grams of stearic acid were combined in a 1 liter beaker and heated to 80° C. 300 grams of aqueous Aluminum-Zirconium Tetrachlorohydrex-Gly (35% solids) was added to the stearic acid solution, with agitation. The mixture was heated for approximately 1 hour, while evaporating off the water, maintaining a temperature around 100° C. The reaction was stopped when the pot temperature reached approximately 110° C. and no more water was observed to be evaporating off. The mixture was then vacuum filtered (while hot, ~112° C.). using a Buchner funnel, to recover the encapsulated aluminum- zirconium salt.

The encapsulated aluminum-zirconium salt appeared to be spherical and were white in color.

EXAMPLE 2

300 grams of a mixture comprised of octamethylcyclotetrasiloxane and decamethylcyclopentasiloxane and 11.88 grams of stearic acid were combined in a 1L round bottom flask equipped with a paddle-blade agitator, a water cooled condenser and a 1 L round bottom receiver and heated to 67° C. 300 grams of aqueous Aluminum-Zirconium Tetrachlorhydrex-Gly (35% solids), heated to 70° C., was added to the stearic acid solution, with agitation. The mixture was heated for approximately 2.25 hours, while distilling off the water, maintaining a temperature around 110° C. The reaction was stopped when the pot temperature reached approximately 122° C. and no more water was observed to be distilling off. The mixture was then vacuum filtered (while hot, ~122° C.), using a Buchner funnel, to recover 108.6 grams of the encapsulated aluminum-zirconium salt. The beads were re-dispersed in 100 grams of a mixture comprised of octamethylcyclotetrasiloxane and decamethylcyclopentasiloxane and heated to 70° C. and filtered again. 104.1 grams of encapsulated aluminum- zirconium salt was recovered after the second filtration.

The encapsulated aluminum-zirconium salts were mostly spheres of varying sizes.

EXAMPLE 3

300 grams of a mixture comprised of octamethylcyclotetrasiloxane and decamethylcyclopentasiloxane and 13.86 grams of stearic acid were combined in a 1 L beaker and heated to 70° C. 300 grams of aqueous Aluminum-Zirconium Tetrachlorhydrex-Gly (35% solids) was added to the stearic acid solution, with agitation. The mixture was heated for approximately 2 hours, while evaporating off the water, maintaining a temperature around 100° C. The reaction was stopped when the pot temperature reached approximately 112° C. and no more water was observed to be evaporating off. The mixture was then vacuum filtered (while hot, ~112° C.), using a Buchner funnel to recover the encapsulated aluminum-zirconium salts.

EXAMPLE 4

150 grams of a mixture comprised of octamethylcyclotetrasiloxane and decamethylcyclopentasiloxane and 6.3 grams of caprylic acid were combined in a 500 ml round bottom flask equipped with a paddle-blade agitator, a water cooled condenser an a 250 ml round bottom receiver. 150 grams of aqueous Aluminum-Zirconium Tetrachlorhydrex-Gly (35% solids) was added to the caprylic acid solution, with agitation. The mixture was heated for approximately 4 hours, while distilling off the water, maintaining a temperature around 110° C. The reaction was stopped when the pot temperature reached approximately 130° C. and no more water was observed to be distilling off. The mixture was cooled and vacuum filtered using a Buchner funnel, to recover the encapsulated aluminum-zirconium salt.

EXAMPLE 5

150 grams of a mixture comprised of octamethylcyclotetrasiloxane and decamethylcyclopentasiloxane and 6.3 grams of iso-stearic acid were combined in a 500 ml round bottom flask equipped with a paddle-blade agitator, a water cooled condenser an a 250 ml round bottom receiver. 150 grams of aqueous Aluminum-Zirconium Tetrachlorhydrex-Gly (35% solids) was added to the iso-stearic acid solution, with agitation. The mixture was heated for approximately 4 hours, while distilling off the water, maintaining a temperature around 107° C. The reaction was stopped when the pot temperature reached approximately 127° C. and no more water was observed to be distilling off. The mixture was vacuum filtered (~80° C.) using a Buchner the encapsulated aluminum- zirconium salt.

The encapsulated aluminum-zirconium salts were uniform in size and mostly spherical.

EXAMPLE 6

150 grams of a mixture comprised of octamethylcyclotetrasiloxane and decamethylcyclopentasiloxane and 6.3 grams of behenic acid were combined in a 500 ml round bottom flask equipped with a paddle-blade agitator, a water cooled condenser an a 250 ml round bottom receiver and heated to approximately 75° C. 150 grams of aqueous Aluminum-Zirconium Tetrachlorhydrex-Gly (35% solids) was added to the behenic acid solution, with agitation. The mixture was heated for approximately 4.5 hours, while distilling off the water, maintaining a temperature around 102° C. The reaction was stopped when the pot temperature reached approximately 135° C. and no more water was observed to be distilling off. The mixture was vacuum filtered (~135°) using a Buchner funnel, to recover the encapsulated aluminum-zirconium salt. The particles were mostly spherical and yellow.

EXAMPLE 7

150 grams of a mixture comprised of octamethylcyclotetrasiloxane and decamethylcyclopentasiloxane and 6.3 grams of glyceryl monostearate were combined in a 500 ml round bottom flask equipped with a paddle-blade agitator, a water cooled condenser and a 250 ml round bottom receiver and heated to approximately 70° C. 150 grams of aqueous Aluminum-Zirconium Tetrachlorhydrex-Gly (35% solids) was added to the glyceryl monostearate solution, with agitation. The mixture was heated for approximately 3.5 hours, while distilling off the water, maintaining a temperature around 100° C. The reaction was stopped when the pot temperature reached approximately 130° C. and no more water was observed to be distilling off. The mixture was vacuum filtered (~85°) using a Buchner funnel, to recover the encapsulated aluminum- zirconium salt. The particles were mostly spherical.

EXAMPLE 8

150 grams of a mixture comprised of octamethylcyclotetrasiloxane and decamethylcyclopentasiloxane and 6.3 grams of sodium stearate were combined in a 500 ml round bottom flask equipped with a paddle-blade agitator, a water cooled condenser an a 250 ml round bottom receiver and heated to approximately 90° C. 100 grams of deionized water was added to dissolve the sodium stearate. 150 grams of aqueous Aluminum-Zirconium Tetrachlorhydrex-Gly (35% solids) was added to the sodium stearate solution, with agitation. The mixture was heated for approximately 3.5 hours, while distilling off the water, maintaining a temperature around 105° C. The reaction was stopped when the pot temperature reached approximately 135° C. and no more water was observed to be distilling off. The mixture was vacuum filtered (~99°) using a Buchner funnel, to recover the encapsulated aluminum- zirconium salt.

EXAMPLE 9

300 grams of a polydimethylsiloxane fluid having a viscosity of 50 centistokes and 11.8 grams of stearic acid were combined in a 1 L round bottom flask equipped with a paddle-blade agitator, a water cooled condenser and a 250 ml round bottom receiver and heated to approximately 70° C. 300 grams of aqueous Aluminum-Zirconium Tetrachlorhydrex-Gly (35% solids) was added to the stearic acid solution, with agitation. The mixture was heated for approximately 1.5 hours, while distilling off the water, maintaining a temperature around 100° C. The reaction was stopped when no more water was observed to be distilling off. The mixture was vacuum filtered (~80°) using a Buchner funnel, to recover the encapsulated aluminum-zirconium salt. The particles were yellow.

EXAMPLE 10

150 grams of a polydimethylsiloxane fluid having a viscosity of 10 centistokes and 6.3 grams of stearic acid were combined in a 500 ml round bottom flask equipped with a paddle-blade agitator, a water cooled condenser an a 250 ml round bottom receiver and heated to approximately 75° C. 150 grams of aqueous Aluminum-Zirconium Tetrachlorhydrex-Gly (35% solids) was added to the stearic acid solution, with agitation. The mixture was heated for approximately 3 hours, while distilling off the water, maintaining a temperature around 115° C. The reaction was stopped when the pot temperature reached approximately 135° C. and no more water was observed to be distilling off. The mixture was vacuum filtered (~80° C.) using a Buchner funnel, to recover the encapsulated aluminum-zirconium salt.

EXAMPLE 11

150 grams of a mixture comprised of octamethylcyclotetrasiloxane and decamethylcyclopentasiloxane (cyclomethicone) and 6.3 grams of stearic anhydride were combined in a 500 ml round bottom flask equipped with a paddle-blade agitator, a water cooled condenser and a 250 ml round bottom receiver. The mixture was heated to 85° C. 150 grams of aqueous Aluminum-Zirconium Tetrachlorhydrex-Gly (35% solids) was added to the stearic anhydride solution, with agitation. The mixture was heated for approximately 1.5 hours, while distilling off the water, maintaining a temperature around 106° C. The reaction was stopped when the pot temperature reached approximately 127° C. The mixture was vacuum filtered (~85° C.) using a Buchner funnel, to recover 50.07 grams encapsulated aluminum-zirconium salt.

EXAMPLE 12

150 grams of a mixture comprised of octamethylcyclotetrasiloxane and decamethylcyclopentasiloxane and 6.6 grams of stearoyl chloride were combined in a 500 ml round bottom flask equipped with a paddle-blade agitator, a water cooled condenser and a 250 ml round bottom receiver. The mixture was heated to 85° C. 150 grams of aqueous Aluminum-Zirconium Tetrachlorhydrex-Gly (35% solids) was added to the stearoyl chloride acid solution, with agitation. The mixture was heated for approximately 2 hours, while distilling off the water, maintaining a temperature around 105° C. The reaction was stopped when the pot temperature reached approximately 130° C. The mixture was vacuum filtered (85° C.) using a Buchner funnel, to recover 57.34 grams of encapsulated aluminum-zirconium salt.

EXAMPLE 13

Four experiments were conducted to determine the effect of agitation rate on particle size. In the experiments 150 grams of a mixture comprised of octamethylcyclotetrasiloxane and decamethylcyclopentasiloxane and 6.3 grams of stearic acid were combined in a 500 ml round bottom flask equipped with a paddle-blade agitator, a water cooled condenser and a 250 ml round bottom receiver and heated to 75° C. 150 grams of aqueous Aluminum-Zirconium Tetrachlorhydrex-Gly (35% solids), was added to the stearic acid solution, with agitation. The mixture was heated while distilling off the water. The agitation during the distillation was maintained at various levels given in Table 1. The reaction was stopped when there was no more water observed to be distilling off. The mixture was then vacuum filtered using a Buchner funnel, to recover the encapsulated aluminum-zirconium salt. The particle size of the resulting encapsulated aluminum-zirconium salts was measured using a Malvern 3600 EZ particle sizer. Results are given in Table 1.

TABLE 1

| Agitation Speed | Particle Size Distribution | (microns) Average |
|---|---|---|
| 150 | 113 to 262 | 199 |
| 200 | 125 to 270 | 199 |
| 400 | 25 to 270 | 130 |
| 650 | 7 to 65 | 27 |

EXAMPLE 14

An suspension stick composition was produced by heating 55 parts of cyclomethicone and 20 parts of stearyl alcohol to 65° C. with stirring. 2 parts of PPG-14 Butyl Ether was then added with continued stirring followed by 1 part of hydrogenated caster oil, 2 parts of talc and 20 parts of an encapsulated aluminum-zirconium salt produced as in Example 1. The mixture was cooled to 53° C. and cast into a stick.

EXAMPLE 15

An aerosol composition was produced by mixing 12 parts of an encapsulated aluminum-zirconium salt as produced in Example 1 with 10.5 parts of cyclomethicone and 2 parts of dimethicone. This mixture was loaded into an aerosol container and charged with 75.5 parts of propellant.

What is claimed is:
1. An aerosol composition comprising
 (A) 1% to 20% by weight of an encapsulated aluminum-zirconium salt composition comprising
  (I) an aluminum-zirconium salt selected from the group consisting of aluminum-zirconium halohydrates; contained in a shell comprising
  (II) a carboxylate or mixture of carboxylates selected from the group consisting of carboxylates having the formula

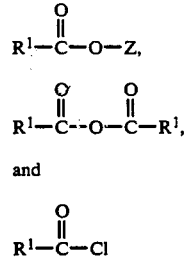

wherein $R^1$ is selected from the group consisting of a saturated or unsaturated, branched or linear alkyl group consisting of at least 2 carbon atoms, a phenyl group, and a phenyl ethylene group; and Z is selected from the group consisting of hydrogen atoms, alkali metals, glyceryl and mixtures thereof;
 (B) 50% to 90% by weight of propellant; and
 (C) 5% to 15% by weight of an anhydrous carrier liquid.
2. The aerosol composition as claimed in claim 1 wherein the composition is comprised of 8% to 12% by weight of the encapsulated aluminum-zirconium salt.
3. A stick composition comprising
 (A) 1% to 20% by weight of an encapsulated aluminum-zirconium salt composition comprising
  (I) an aluminum-zirconium salt selected from the group consisting of aluminum-zirconium halohydrates; contained in a shell comprising
  (II) a carboxylate or mixture of carboxylates selected from the group consisting of carboxylates having the formula

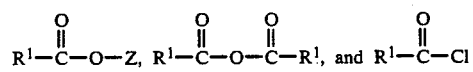

wherein $R^1$ is selected from the group consisting of a saturated or unsaturated, branched or linear alkyl group consisting of at least 2 carbon atoms, a phenyl group, and a phenyl ethylene group; and Z is selected from the group consisting of hydrogen atoms, alkali metals, glyceryl and mixtures thereof;
 (B) 20% to 65% by weight of a carrier fluid; and
 (C) 5% to 30% by weight of a gellant.
4. A roll-on composition comprising
 (A) 1% to 20% by weight of an encapsulated aluminum-zirconium salt composition comprising
  (I) an aluminum-zirconium salt selected from the group consisting of aluminum-zirconium halohydrates; contained in a shell comprising
  (II) a carboxylate or mixture of carboxylates selected from the group consisting of carboxylates having the formula

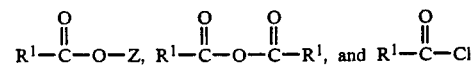

wherein $R^1$ is selected from the group consisting of a saturated or unsaturated, branched or linear alkyl group consisting of at least 2 carbon atoms, a phenyl group, and a phenyl ethylene group; and Z is selected from the group consisting of hydrogen atoms, alkali metals, glyceryl and mixtures thereof; and
 (B) 60% to 90% by weight of a carrier fluid.

* * * * *